(12) United States Patent
Gerwick, III et al.

(10) Patent No.: US 7,393,812 B2
(45) Date of Patent: Jul. 1, 2008

(54) METHYLIDENE MEVALONATES AND THEIR USE AS HERBICIDES

(75) Inventors: Ben Clifford Gerwick, III, Carmel, IN (US); Paul Richard Graupner, Carmel, IN (US); Stephen Craig Fields, Indianapolis, IN (US); Paul Richard Schmitzer, Indianapolis, IN (US); William Kirkland Brewster, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 193 days.

(21) Appl. No.: 11/282,433

(22) Filed: Nov. 18, 2005

(65) Prior Publication Data

US 2006/0111241 A1    May 25, 2006

Related U.S. Application Data

(60) Provisional application No. 60/629,736, filed on Nov. 19, 2004.

(51) Int. Cl.
*A01N 37/00* (2006.01)
*C07C 59/10* (2006.01)
(52) U.S. Cl. .................. 504/320; 562/587; 514/557
(58) Field of Classification Search ............... 504/116.1
See application file for complete search history.

(56) References Cited

OTHER PUBLICATIONS

Lange et al, Plant Physiology, Isoprenoid Biosynthesis. Metabolite profiling of Peppermint Oil Gland Secretory Cells and Application to Herbicide Target Analysis, 2001, 127(1), pp. 305-314.*

* cited by examiner

*Primary Examiner*—Paul A Zucker
(74) *Attorney, Agent, or Firm*—Craig Mixan

(57) ABSTRACT

Methylidene mevalonic acid, a material isolated from a fungal extract, and its primary alcohol and carboxylic acid derivatives, are potent herbicides demonstrating a broad spectrum of weed control. These materials are useful for weed control and for the cultivation of organically grown crops.

4 Claims, No Drawings

METHYLIDENE MEVALONATES AND THEIR USE AS HERBICIDES

This application claims benefit of U.S. Ser. No. 60/629,736, filed Nov. 19, 2004.

BACKGROUND OF THE INVENTION

This invention relates to novel methylidene mevalonate and its derivatives and to the use of these compounds as herbicides.

Organic farming is an increasingly important means of production of food and fiber. As with all types of agriculture, control of weeds and pests is important to the yield and value of the crop. Pest control products suitable for organic farming are generally bio-organic in origin. New pest control products for agriculture, and specifically for organic farming, are important additions to the field. Thus it is highly desirable to discover natural compounds that would allow the organic farmer to more effectively control weeds.

SUMMARY OF THE INVENTION

It has now been found that methylidene mevalonate (3-hydroxy-4-(hydroxymethyl)-3-methylpent-4-enoic acid) and its derivatives are potent herbicides with a broad spectrum of weed control. The invention includes compounds of Formula I:

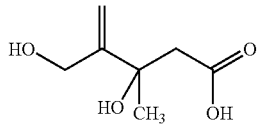

(I)

and agriculturally acceptable derivatives of the carboxylic acid and the primary alcohol functionalities and their enantiomers.

The invention includes herbicidal compositions comprising an herbicidally effective amount of methylidene mevalonate of Formula I:

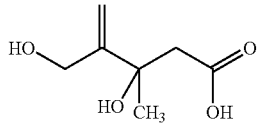

(I)

and agriculturally acceptable derivatives of the carboxylic acid and the primary alcohol functionalities and their enantiomers in admixture with an agriculturally acceptable adjuvant or carrier. The invention also includes a method of use of these compounds and compositions to kill or control undesirable vegetation by application of an herbicidal amount of the compound to the vegetation or to the locus of the vegetation.

Another aspect of this invention is a process for producing an extract containing the compound of Formula I which comprises culturing *Fusarium* sp. strain DA056446 or *Nodulisporium* sp. DA092917 in a suitable medium and extracting the compound from the mycelia and growth medium with suitable solvents. Suitable growth medium include but are not limited to Malt Extract Agar (Becton Dickenson, Sparks, Md.) and Oatmeal Agar (Becton Dickenson, Sparks, Md.). Suitable solvents include but are not limited to 50% aqueous ethanol and methanol. The extracts may be further concentrated or purified by techniques well known in the art such as column chromatography.

Another aspect of this invention is a method of using of the concentrated extracts isolated from culturing *Fusarium* sp. strain DA056446 or *Nodulisporium* sp. DA092917 to kill or control undesirable vegetation by application of the concentrated extract to the vegetation or to the locus of the vegetation.

Yet another aspect of this invention is a process for producing a compound of Formula I

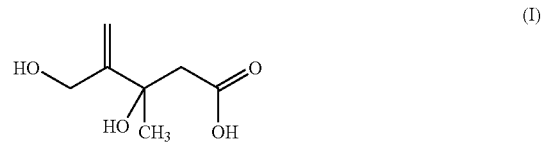

(I)

which comprises the steps of:

a) condensing methyl vinyl ketone 2 with formaldehyde in the presence of a base to provide the hydroxy ketone adduct 3,

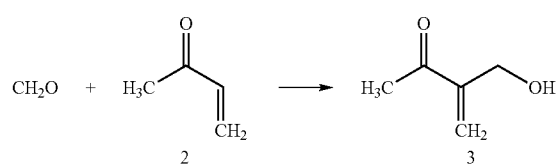

b) reacting 3 with 2 equivalents of lithio tert-butyl acetate to give the tert-butyl ester 4,

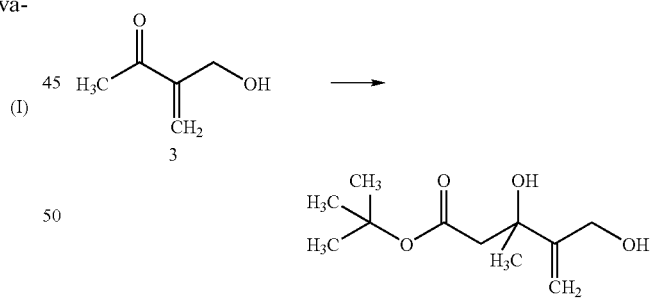

c) treating ester 4 with neat trifluoroacetic acid to give lactone 5,

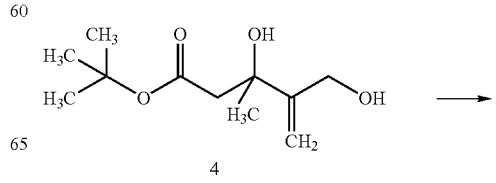

-continued

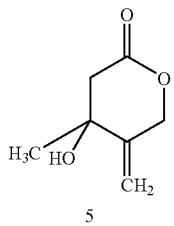

5 d) treating lactone 5 with aqueous base to give the carboxylate salt 6, and

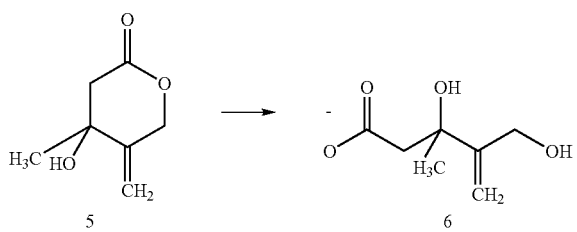

e) neutralizing 6 with acid to provide methylidene mevalonic acid 1.

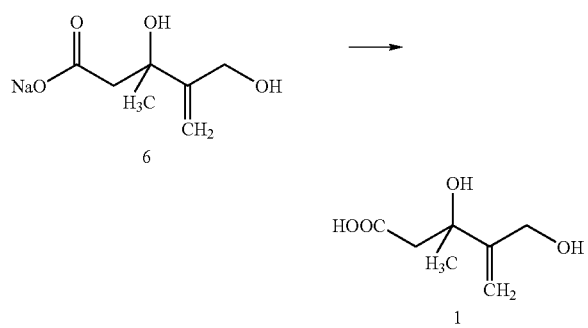

DETAILED DESCRIPTION OF THE INVENTION

The herbicidal compounds of the present invention are derivatives of methylidene mevalonate (Formula I):

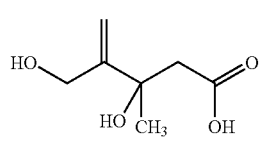

The carboxylic acid of Formula I is believed to be the compound that actually kills or controls undesirable vegetation and is typically preferred. Analogs of this compound in which the acid group is derivatized to form a related substituent that can be transformed within plants or the environment to the acid group possess essentially the same herbicidal effect and are within the scope of the invention. Therefore, an "agriculturally acceptable derivative", when used to describe the carboxylic acid functionality, is defined as any salt, ester, amide or any other acid derivative well known in the art which (a) does not substantially affect the herbicidal activity of the active ingredient and (b) is or can be hydrolyzed in plants or soil to the acid of Formula I that, depending upon the pH, is in the dissociated or the undissociated form. The preferred "agriculturally acceptable derivatives", when used to describe the carboxylic acid functionality are salts, esters and amides and the lactone.

Suitable salts include those derived from alkali or alkaline earth metals and those derived from ammonia and amines. Preferred cations include sodium, potassium, magnesium, and aminium cations of the formula:

$$R_1R_2R_3NH^+$$

wherein $R_1$, $R_2$, and $R_3$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_1$, $R_2$, and $R_3$ are sterically compatible. Additionally, any two of $R_1$, $R_2$, and $R_3$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Suitable esters include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethyl-hexanol, butoxyethanol, methoxypropanol, allyl alcohol, propargyl alcohol or cyclohexanol. The methyl ester can be made using $TMSCHN_2$ or $CH_2N_2$ in MeOH. Other delicate reagents known to those experienced in the art can similarly be used to prepare higher esters (e.g. $Bn(TMS)CHN_2$ for the benzyl ester). Suitable amides include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallyl-amine, 2-butoxyethylamine, morpholine, cyclododecylamine, or benzylamine. The amides can be prepared from the methylidene mevalonic lactone by reaction with an amine in methanol.

Other suitable agriculturally acceptable derivatives include the lactone derived from methylidene mevalonate:

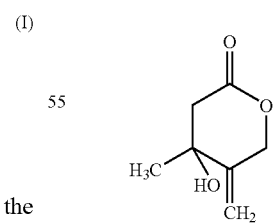

Since methylidene mevalonate contains an asymmetric carbon atom, it can exist as a racemic mixture or as distinct enantiomers, i.e., mirror image isomers that are not superimposable on one another.

The terms "alkyl", "alkenyl" and "alkynyl", as used herein, include within their scope straight chain, branched chain and cyclic moieties. The terms "alkenyl" and "alkynyl" are intended to include one or more unsaturated bonds.

The primary alcohol group, like the carboxylic acid group, can be derivatized to form a related substituent that can be transformed within plants or the environment back to a primary alcohol group. Therefore, an "agriculturally acceptable derivative", when used to describe the primary alcohol functionality, is defined as any ether, ester or any other alcohol derivative well known in the art which (a) does not substantially affect the herbicidal activity of the active ingredient and (b) is or can be hydrolyzed in plants or soil to the alcohol of Formula I. Such derivatives capable of breaking down into the alcohol include ethers, silyl ethers, esters, sulfonate esters, phosphate esters, carbonates or carbamates. These derivatives can be prepared by the reaction of the primary alcohol in compound 4 with, for example, a suitable acid halide, acid anhydride, chloroformate, carbamyl chloride, sulfonyl chloride, silyl chloride or chlorophosphate, followed by cleavage of the tert-butyl ester.

Methylidene mevalonate was identified as the principal phytotoxic component of fungal fermentation broths DA056446.0 and DA092917.0 supplied by MYCOsearch (now MycoSynthetix Inc.) under an Extract Supply Agreement with Dow AgroSciences. The original samples exhibited control in a *Lemna* and *Agrostis* screen and dereplication indicated the presence of no other herbicides. The active component was isolated by bio-assay directed isolation procedures and the structure was determined by NMR spectroscopy and was confirmed by independent synthesis.

The novel fungal strains *Fusarium* sp. DA056446 and *Nodulisporium* sp. DA092917 were isolated at MYCOsearch (now Mycosynthetix, Inc. 4905 Pine Cone Drive, Durham, N.C.). These strains have been deposited in accordance with the terms of the Budapest Treaty at the National Center for Agricultural Utilization Research, 815 North University Street, Peoria, Ill. The strains have been assigned deposit numbers NRRL 30882 (DA056446) and NRRL 30883 (DA092917).

Strain DA056446 grows slowly with limited aerial mycelia and produces a dark reddish-orange pigment on Potato Dextrose Agar (PDA) and Malt Extract Agar. Microscopically, strain DA056446 produces branched hyphae and boat-shaped, 4-5 cell macroconida with a tapered apical cell at each end. This morphology is consistent with the fungi of the genus *Fusarium*. Strain DA092917 produced abundant white vegetative mycelium and black aerial mycelium on PDA and white mycelium with no aerial mycelium on Oatmeal Agar. No spores or conidia were evident on either media. Strains DA056446 and DA092917 were submitted to MIDI Labs (Newark, Del.) for partial DNA sequencing of the large subunit ribosomal RNA gene. The DNA sequence was compared to the GenBank database using the BLASTN algorithm (http://www.ncbi.nlm.nih.gov/BLAST/). The strongest BLAST matches for strain DA056446 were various *Fusarium* species. The strongest BLAST matches for strain DA092917 was *Hypoxylon mammatum* and *Hypoxylon serpens*. The anamorph of *Hypoxylon* is *Nodulisporium*, which is consistent with the cultured strain DA092917. Therefore, the two strains were designated *Fusarium* sp. DA056446 and *Nodulisporium* sp. DA092917.

Methylidene Mevalonate Synthesis

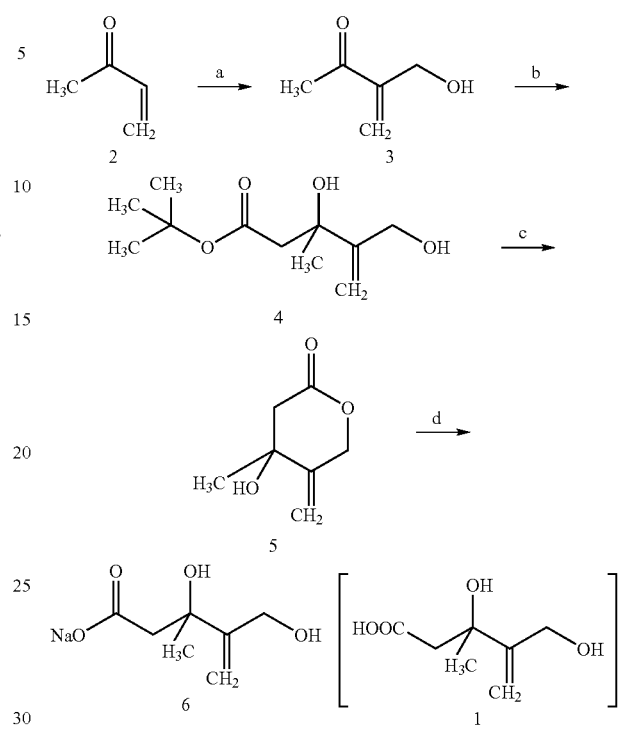

a. 37% $CH_2O$, aq., 0.1 DABCO, 1,4-dioxane, 0° C.; b. 2 LDA+2 tert-butyl acetate, −78° C.; c. $CF_3COOOH$, 25° C.; d. 1N NaOH, aq.

Condensation of methyl vinyl ketone (2) with formaldehyde in the presence of a base provided the hydroxy ketone adduct 3 in 60% yield after vacuum distillation. Reaction of 3 with 2 equivalents of lithio tert-butyl acetate gave 4, the tert-butyl ester of the natural product in racemic form, in 50% yield after radial chromatography. Treatment of ester 4 with neat trifluoroacetic acid (TFA) followed by evaporation of volatiles in vacuo gave NMR pure lactone 5 in near quantitative yield. Lactone 5 was quantitatively converted to the racemic form of the carboxylate salt 6 of the natural product upon treatment with 1N NaOH. Neutralization of 6 with acid provided racemic methylidene mevalonic acid which proved to be spectroscopically identical to the natural material.

The individual methylidene mevalonic acid enantiomers were prepared via the process of synthesis and chromatographic separation of the diastereomeric (R)-Mosher's esters ((R)-α-methoxy-α-(trifluoromethyl)-phenylacetates) followed by chemical cleavage of the esters.

The compounds of Formula I have been found to be useful post-emergence herbicides. They are generally employed to control a broad spectrum of the vegetation in an area. Areas of application include pasture and rangelands, roadsides and rights of ways.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include emerging seedlings and established vegetation.

Herbicidal activity is exhibited by the compounds of the present invention when they are applied directly to the plant or to the locus of the plant at any stage of growth after emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art. Generally, it is preferred to apply the compounds of Formula I postemergence to relatively immature undesirable vegetation to achieve the maximum control of weeds.

Application rates of about 125 to about 4,000 g/Ha are generally employed in postemergence operations.

The herbicidal compounds of the present invention are often best applied in conjunction with one or more other organic herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include pelargonic acid and other $C_7$-$C_{22}$ alkanoic fatty acids. Such fatty acids may be saturated or unsaturated, branched or unbranched monocarboxylic acids and their agronomically acceptable salts, esters and epoxides. It is generally preferred to apply the compounds of the invention and other complementary herbicides at the same time, either as a combination formulation or as a tank mix.

While it is possible to utilize the compounds of Formula I directly as herbicides, it is preferable to use them in mixtures containing a herbicidally effective amount of the compound along with at least one agriculturally acceptable adjuvant or carrier. Suitable adjuvants or carriers should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLE 1

1. Discovery of Activity.

Fungi samples, specifically samples derived from strain DA056446.0, were received in 96 shallow or deep well microtiter master plates. Each shallow well master plate contained 1.6 ml equivalent of dried test material. To each shallow well master plate was added 160 µl of methanol followed by sonication to create a soluble test sample. Robotically, 80 µl of the sample was transferred to a second shallow well plate (daughter plate) and 120 µl of 50% methanol was added to create a 1:2.5 dilution. A robot was used to transfer 100 µl of this diluted sample from the daughter plate to a 96 well "bubble tray" (38.5 cm×32 cm×2 cm). The samples were air dried prior to testing.

*Lemna* and *Agrostis* were used as test species. *Lemna* was grown to the 4-leaf stage in a Conviron growth chamber (16 hr photoperiod, 29° C.) prior to testing. The growth media ("*Lemna* media") consisted of 3.1 gm/L Gamborg's B-5 Basal salt mixture, 4.4 gm/L Murahige and Skoog modified basal salt mixture (NH$_4$-Free) and 10 gm/L sucrose, pH adjusted to 5.5. *Agrostis* was added to the screen as ungerminated seeds. To 1,500 ml of *Lemna* media (less sucrose) 5 ml of *Agrostis* seed was added and placed on a table top stirrer. A Wheaton Unispense was used to dispense 2.0 ml of *Lemna* media into each bubble tray. The *Lemna* was added to each test well at this point using a sterile loop. The bubble trays were maintained in a Conviron growth chamber (16 hr. photoperiod, 19° C.) for seven days after which visual observations were made on a 0 to 100 scale, where 0 represents no injury and 100 represents complete necrosis. Sample DA 056446.0 was sufficiently active in the *Lemna/Agrostis* screen to warrant further investigation.

2. Isolation of Active.

One liter of freeze dried methanol extract of culture DA056446.0 was partitioned between n-butanol and water (pH=4.5). Bioassay of aliquots from these solvents confirmed highest activity in the aqueous fraction. The aqueous fraction was dried, redissolved in 20% methanol, and fractionated on a preparative C-18 column (particle size, 10 µm; column size, 40 cm×2 cm; mobile phase, 100% of 10 mM NH$_4$ acetate to 50% acetonitrile in 15 minutes; flow rate, 10 ml/min; uv detection at 210 nm). Activity was localized to two regions by bioassay, either using the methods described above for *Lemna* and *Agrostis*, or by direct application of dried and resuspended fractions on whole plant seedlings. The fraction containing the more polar active was dried and rechromatographed on C-8 AQS (particle size, 5 µm; column size, 15 cm×4.6 mm; mobile phase, 0.05% aqueous TFA; flow rate, 1 ml/min; detection, uv at 210 nm) in 1 mg aliquots. The activity was localized to a peak with retention time of 6.0 minutes. The sample was collected, dried, and rechromatographed under identical conditions to yield ~1 mg of clear solid. This was submitted directly for NMR and MS analysis.

The fraction containing the later eluting active from preparative chromatography was only weakly active. Nevertheless, it was pursued by fractionation on a C-18 analytical BDS column (particle size, 5 µm; column size, 25 cm×4.6 mm; mobile phase 5% aqueous TFA (0.05%) to 80% acetonitrile in 25 minutes; flow rate 1 ml/min; detection, uv at 210 nm). Bioassay of chromatography fractions indicated activity in two regions; surprisingly, one of the active regions corresponded to the polar active previously isolated. Apparently the non-polar active was partially converted to the polar active during chromatography.

3. Identification of Active.

All NMR spectra were recorded on a Bruker DRX400 spectrometer, operating at 400.13 MHz ($^1$H), and 100.62 MHz ($^{13}$C), and equipped with either a 3 mm micro inverse probe, or a 3 mm micro dual probe (Nalorac). Typically, the samples were dissolved in 140 µl of deuterium oxide (D$_2$O), and were referenced to the residual proton solvent resonances at 4.7 ppm. For $^{13}$C spectra, the samples were referenced to external standards.

Proton spectra consisted of 32K data points acquired over a sweep width of 5995 Hz, giving a resolution of 0.18 Hz/pt, no window was used prior to Fourier transformation. If required, the residual water (HOD) signal was suppressed using presaturation (65 dB for 1.5 sec) prior to spectrum acquisition. The number of transients was set to ensure adequate signal to noise (s/n) for each individual sample.

Carbon 1D spectra consisted of 64 k points acquired over a sweep width of 25,000 Hz, giving a resolution of 0.4 Hz/pt.

Line broadening (0.1 Hz) was applied prior to Fourier transformation. DEPT-135 analysis was used in order to sort the multiplicity of the individual carbon signals.

Carbon/hydrogen (C/H) correlation experiments were acquired in the inverse mode (proton detection) on these samples, using the HMQC pulse sequence. 256 experiments were acquired, consisting of 2k data points in the proton dimension. GARP decoupling was used to remove proton coupling in the carbon dimension. Fourier transform in F2 ($^1$H, using a squared cosine window) and linear prediction in F1 ($^{13}$C) was used resulting in a final dataset size of 2K×512.

Long range C/H correlations to quaternary carbon atoms were made using the HMBC pulse sequence as supplied as part of the Xwinnmr package. The pulse seqence was optimized for 8 Hz long range coupling, which typically results in cross peaks over 2-3 bonds. Acquisition and processing parameters used were identical to those described for HMQC experiments.

The proton spectrum and the carbon spectrum of the isolated active compounds were as follows:

| Assignment | $^1$H (in D$_2$O) ppm | $^{13}$C (in D$_2$O), ppm |
| --- | --- | --- |
| 1 | — | 176 (s) |
| 2 | 2.6 (1H, d, 15 Hz) | 45 (t) |
|   | 2.5 (1H, d, 15 Hz) |  |
| 3 | — | 73 (s) |
| 4 | — | 152 (s) |
| 5 | 4.1 (2H, s) | 61 (t) |
| 6 | 1.3 (3H, s) | 27 (q) |
| 7 | 5.1 (1H, s) | 109 (t) |
|   | 5.0 (1H, s) |  |

The structure was determined in the following manner. Proton NMR indicates that the molecule contains 3 methylene groups, one of which is split into a pair of doublets ($^2J_{HH}$=15 Hz)—indicating a chiral center in close proximity—and a methyl group. The carbon spectrum indicates that the two signals at 5.1 ppm are due to a terminal olefin methylene (at 109 ppm), where the germinal coupling between the two protons is ca. 0 Hz.

DEPT analysis revealed that the peaks of 109, 61, and 45 ppm correlate to the 3 methylenes, indicating an olefin, and an oxygen substituted methylene. An HMQC experiment showed that the coupled methylene correlated to the carbon signal at 45 ppm, indicating carbon attachments to this carbon. The rest of the spectrum indicate another olefinic carbon at 152 ppm (no proton attachments), a carbonyl at 176 ppm (probably a carboxylic acid), an aliphatic quaternary atom at 73 ppm (with one oxygen attachment) and the methyl at 27 ppm.

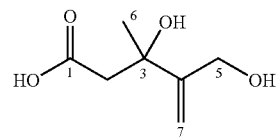

Mass spectral characterization indicated a very strong— ESI signal correlating to a MW of 160. The negative ionization was good evidence for the carboxylic acid function. The NMR evidence shows 7 carbon atoms, and at least 9 protons.

The carboxylic acid adds 2 oxygen atoms, and a further proton. This accounts for 126 amu. The remaining 34 amu may be accounted for with 2 hydroxy groups, giving a molecular formula of $C_7H_{12}O_4$.

The molecule was assembled by analysis of a single HMBC experiment (optimized for 8 Hz coupling). The methyl protons correlated to the quaternary olefinic carbon, the quaternary aliphatic carbon atom, and the methylene at 45 ppm. The lack of coupling and the chemical shift of this methyl singlet indicate that it is connected to the quaternary aliphatic carbon atom, which has a hydroxy substituent on it. Cross peaks arising from the protons connected to the carbon at 45 ppm confirm this, and also indicate that the carboxylic acid is connected to this methylene. The other methylene carbon at 63 ppm—indicating the attachment of the second hydroxy group—shows cross-peaks to both of the olefinic carbon atoms. These correlations are consistent with the structure of methylidene mevalonate.

Closer evaluation of the proton spectrum indicated a second component in the sample, at about 5% of the total sample amount. The acid as drawn may be expected to readily form the lactone, and may exist in an equilibrium between the two forms. This observation explains the identity and interconversion of active components isolated from the crude fermentation extract (see Section 2 above on isolation of active). The lack of an HMBC cross-peak between the methylene singlet and the carbonyl oxygen, indicates that in aqueous solution at neutral pH (the conditions that the NMR spectra were acquired), the open chain form is the preferred conformation.

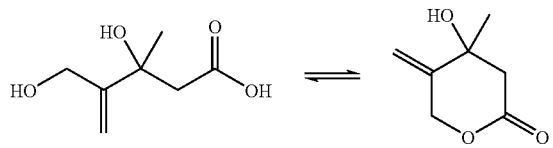

4. Synthesis of 4-Methylidene Mevalonate

A. 2-Hydroxymethyl-1-buten-3-one

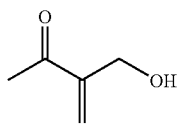

In a 1 L round bottom flask, methyl vinyl ketone (83.2 mL, 1 mol) was dissolved in THF (500 mL) and cooled to 0° C. under a nitrogen atmosphere. Formaldehyde (37 wt % aq. solution, 75 mL, 1.2 mol) was added with magnetic stirring. Dabco (11.2 g, 0.1 mol) then was added, while keeping the temperature below 2° C. Within 4 h, the reaction was complete as assessed by TLC and GC. The reaction was poured into brine (500 mL) and the layers were separated. The brine was extracted with diethyl ether (3×100 mL), and the organic layers pooled and re-washed with brine (500 mL). The brown organic layer was treated with $MgSO_4$ and suction filtered through a small silica gel/Celite plug. After solvent removal (rotary evaporator), the residue (99 g) was purified by vacuum distillation (55° C., 0.7-1.0 Torr) to provide 49.4 g of 2-hydroxymethyl-1-buten-3-one (49% yield), which was blanketed with nitrogen, and immediately placed in a refrigerator at 4° C.

ms: 99/100 (2%), 85 (100%, M$^+$-15)
$^1$H NMR (ppm; CDCl$_3$): 6.12 (s, 1H), 6.04 (m, 1H), 4.32 (d, 1H), 4.30 (s, 1H), 2.37 (m, 4H)

B. Tert-Butyl methylidene mevalonate

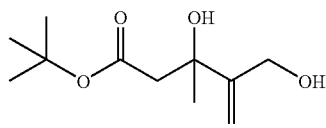

Diisopropylamine (8.2 mL, 63 mmol) was dissolved in THF (Aldrich Sure Seal, 75 mL) and cooled to −78° C. in a 3-necked round bottom flask equipped with magnetic stir bar, dry N$_2$ line and thermocouple for temperature monitoring. n-Butyl lithium (2.5 M solution in hexane, 25.2 mL, 63 mmol) was added via syringe at a rate such that the temperature did not exceed −60° C. The cooling bath was removed and replaced with an ice-water bath. After the temperature reached 0° C., the reaction mixture again was cooled to −78° C. Tert-Butyl acetate (8.48 mL, 63 mmol) was added at a rate such that the temperature did not exceed −60° C. After 30 min, 2-hydroxymethyl-1-buten-3-one (3.0 g, 30 mmol) was added dropwise at a rate such that the temperature did not exceed −60° C. The reaction was complete after 30 min, as assessed by TLC and GC. The reaction was quenched by addition of 10% aq. citric acid (75 mL) and the layers were separated. The aqueous layer was extracted with diethyl ether (3×15 mL), and the organic layers were pooled and washed with brine (100 mL). The organic layer was treated with Na$_2$SO$_4$ and suction filtered through a small silica gel/Celite plug. The solvent was removed by rotary evaporation to give 6.87 g product (95.5% pure by GC). The crude product was purified by MPLC (silica gel, 10→50% EtOAc/Hex) to provide 5.0 g of tert-butyl methylidene mevalonate (77% yield), pure by GC.

ms: 201 (2%, M$^+$-15), 159/160, 145, 124, 101, 85, 57.
$^1$H NMR (ppm; CDCl$_3$): 5.11 (s, 1H), 5.07 (s, 1H), 4.50 (s, 1H), 4.24 (bs, 2H), 2.74 (d, 2H; J=15.8 Hz), 2.50 (bd, 3H, J=15.8 Hz), 1.45 (s, 9H), 1.39 (s, 3H).

C. Methylidene Mevalonolactone

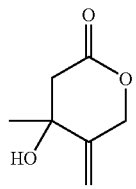

Trifluoroacetic acid (40 mL) and anisole (8.0 mL, 74 mmol) were added to a 0.5 L round bottom flask equipped with magnetic stir bar and drying tube. After cooling to 0° C., tert-butyl methylidene mevalonate (8.2 g, 38 mmol) was added dropwise over 10 min, via a pressure-equalizing addition funnel. After 5 min, the ice bath was removed, and after another 5 min, the volatiles were removed by rotary evaporation. The oily brown residue was purified by MPLC (silica gel column in Elution Solution system, 50% EtOAc/Hex), providing 4.4 g (82% yield) of methylidene mevalonolactone (96% pure by GC).

ms: 143 (<1%, M+), 99, 85, 71, 55.

$^1$H NMR (ppm; CDCl$_3$): 5.43 (t, 1H, J=1 Hz), 5.23 (t, 1H, J=1.4 Hz), 4.95 (dt, 1H, J$_a$=13.5 Hz, J$_b$=1.3 Hz), 4.76 (dt, 1H, J$_a$=13.5 Hz, J$_b$=1.3 Hz), 2.80 (d, 1H; J=16.1 Hz), 2.68 (d, 1H, J=16.1 Hz), 2.17 (bs, 1H), 1.50 (s, 3H).

$^{13}$C NMR (ppm): 170.621, 145.049, 112.299, 70.504, 69.624, 45.251, 27.814.

D. 4-Methylidene Mevalonate, Sodium Salt

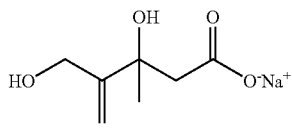

Methylidene mevalonolactone (1.0 g, 7 mmol) was dissolved in 1 N NaOH (7.0 mL, 7.0 mmol) in a 50 mL round bottom flask at 25° C. After 2 h, the solvent was removed by rotary evaporation. After 72 hours under high vacuum, the sodium salt of methylidene mevalonate was obtained as a sticky orange gum in approximately quantitative yield, 95 wt % according to NMR integration. The material became a crystalline orange solid upon standing.

$^1$H NMR (ppm; D$_2$O): 5.20 (s, 1H), 5.15 (s, 1H), 4.19 (s, 2H), 2.60 (d, 1H; J=15.1 Hz), 2.47 (d, 1H, J=15.1 Hz), 1.35 (s, 3H).

$^1$H NMR (ppm; DMSO-d$_6$): 7.99 (s, 1H), 4.98 (m, 1H), 4.92 (m, 1H), 4.71 (t, 1H, J=5.4 Hz), 3.99 (d, 2H, J=4.9 Hz), 2.20 (d, 1H, J=14.8 Hz), 2.00 (d, 1H, J=14.5 Hz), 1.14 (s, 3H).

$^{13}$C NMR (ppm; DMSO): 176.206, 156.553, 105.638, 71.446, 60.686, 47.392, 28.908.

5. Synthesis of 4-Methylidene Mevalonate Enantiomers

A. Tert-Butyl 4-methylidene mevalonate, (R)-Mosher's ester

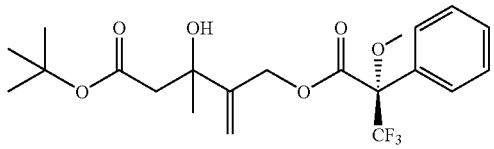

Tert-butyl methylidene mevalonate (0.428 mg, 2.0 mmol) was dissolved in THF (10 mL) with magnetic stirring under a nitrogen atmosphere. To this solution were added diisopropylethylamine (344 μL, 2.0 mmol) and (S)-(+)-α-methoxy-α-(trifluoromethyl)phenylacetyl chloride (0.5 g, 2.0 mmol). The solution was cooled to 0° C., and then 4-pyrrolidinopyridine (0.030 g, 0.2 mmol) was added, resulting in a turbid white reaction mixture. The reaction mixture was warmed to 25° C., stirred for 48 h, then diluted with dichloromethane (10 mL) and stirred an additional 30 min. The volatiles were removed by rotary evaporation, and the residue was partitioned between dichloromethane and water (50 mL each). After separation of the layers, the aqueous fraction was washed with dichloromethane (2×25 mL). The pooled organic fractions were washed with brine (50 mL), dried (MgSO$_4$), filtered through a silica gel/Celite plug, and evaporated to give a thick oily residue. The crude material was purified by radial chromatography (Chromatotron™, 6 mm silica gel rotor, 0-25% EtOAc/hexane eluent) to provide tert-Butyl 4-methylidene mevalonate, (R)-Mosher's ester (0.587 g) in 69% yield.

GC-MS (EI, m/z) 376, 361, 317, 309, 285, 269, 203, 189 (100%), 143, 125, 105, 77, 57; IR (cm$^{-1}$) 2980.5, 1750.7, 1245.3, 1167.9; $^1$H NMR (δ; CDCl$_3$; relative integrals are diastereomeric averages, except as indicated) 7.53 (m, 2H), 7.40 (m, 3H), 5.20 (2s, 1H per diastereomer vinyl), 5.11 (2 m, 1H per diastereomer vinyl), 4.93 (m, 2H), 4.36 and 4.33 (2 s, 1H per diastereomer OH), 3.56 (m, 3H), 2.65 (2d, 1H), 2.45 (d, 1H), 1.43 (2s, 9H per diastereomer tert-butyl), 1.32 (s, 3H); $^{13}$C NMR (δ; CDCl$_3$) 172.11, 172.06, 166.2, 147.7, 147.6, 132.2, 129.6, 128.4, 127.4, 113.0, 112.8, 82.1, 72.7, 65.6, 65.5, 55.5, 45.3, 28.2, 28.1, 28.0; $^{19}$F NMR (δ; CDCl$_3$)-73.836; Anal. Calcd for C$_{21}$H$_{27}$F$_3$O$_6$, C, 58.33; H, 6.29; F, 13.18; Found: C, 58.23; H, 6.29; F, 13.08.

Preparative isolations were performed by dissolving 60 mg of the diasteromeric mixture of (R)-Mosher's esters in 1.5 mL of hexane. Two hundred μl aliquots of the solution were injected onto a Chiralcel OF column (25 cm×4.6 mm ID) and eluted with a solution comprising 2.5% isopropanol/97.5% pentane (V/V) at a flow rate of 1.0 mL/min. The fractions were collected and appropriately combined. The solvent was removed under a nitrogen stream at ambient temperature. Sample purities were assessed by HPLC analysis: peak areas were integrated and stereoisomer ratios were calculated by area percent. Thus, the first eluting diastereomer, designated as A, was obtained in high purity (no detectable diastereomer B), but the second diastereomer, B, was obtained in a 17/83 stereoisomer ratio (A:B). Therefore, all of the impure B product obtained was passed through the chromatographic system again, via the same process. Subsequent HPLC analysis of the combined fractions of B indicated a diastereomeric ratio of 4/96.

"A": $^1$H NMR (δ; CDCl$_3$) 7.53 (m, 2H), 7.41 (m, 3H), 5.20 (s, 1H), 5.12 (t, 1H, J=1.3 Hz), 4.93 (s, 2H), 4.33 (s, 1H), 3.56 (q, 3H, J=1.1 Hz), 2.65 (d, 1H, J=15.6 Hz), 2.45 (d, 1H, J=15.7 Hz), 1.43 (s, 9H), 1.31 (s, 3H); [α]$_D^{20}$ (conc. 1.22, CDCl$_3$)+265.6°.

"B": $^1$H NMR (δ; CDCl$_3$) 7.53 (m, 2H), 7.41 (m, 3H), 5.19 (s, 1H), 5.11 (t, 1H, J=1.4 Hz), 4.99 (dm, 1H, J$_a$=14.5 Hz), 4.87 (dm, 1H, J$_a$=14.3 Hz), 4.37 (s, 1H), 3.56 (q, 3H, J=1.1 Hz), 2.66 (d, 1H, J=15.9 Hz), 2.44 (d, 1H, J=15.9 Hz), 1.42 (s, 9H), 1.31 (s, 3H); [α]$_D^{20}$ (conc. 1.135, CDCl$_3$)+320.7°.

B. (−)-4-Methylidene Mevalonate, Potassium Salt

"A" (0.212 g, 0.49 mmol) was dissolved in methanol (2.0 mL) in a 20 mL screw-cap vial at 25° C., with magnetic stirring. To this solution was added 85% KOH (0.036 g, 0.54 mmol). After 24 h, the solvent was blown off with a nitrogen stream. The product was isolated by partitioning between water (1 mL) and ether (3×1 mL), to remove methyl (S)-(+)-α-methoxy-α-(trifluoromethyl)phenylacetate. The aqueous layer was evaporated to provide (−)-4-methylidene mevalonate, potassium salt (66 mg, 68%), containing a trace of potassium (S)-(+)-α-methoxy-α-(trifluoromethyl)phenylacetate (<2% as determined from NMR integrals).

$^1$H NMR (δ; CD$_3$OD): 5.16 (dd, 1H, J$_a$=1.1 Hz, J$_b$=2.5 Hz), 5.12 (dd, 1H, J$_a$=1.5 Hz, J$_b$=3.2 Hz), 4.18 (m, 2H), 2.56 (d, 1H; J=15.1 Hz), 2.34 (d, 1H, J=15.1 Hz), 1.32 (s, 3H); [α]$_D^{20}$ (conc. 3.28, H$_2$O)−215.5°.

C. (+)-4-Methylidene Mevalonate, Potassium Salt

By the same procedure described immediately above, "B" (0.172 g, 7 mmol) was treated with methanolic KOH (0.029 g) to provide (+)-4-Methylidene mevalonate, potassium salt (0.031 g, 39%) containing a trace of potassium (S)-(+)-α-methoxy-α-trifluoromethyl)-phenylacetate (<4% as determined from NMR integrals).

$^1$H NMR (δ; CD$_3$OD): 5.16 (br d, 1H, J=1.1 Hz), 5.12 (m, 1H), 4.18 (m, 2H), 2.56 (d, 1H; J=15.1 Hz), 2.34 (d, 1H, J=15.1 Hz), 1.32 (s, 3H); $[\alpha]_D^{20}$ (conc. 3.11, H$_2$O)+170.4°.

Biological assays indicate that the herbicidal activity was manifested by only enantiomer B.

of spray solution were applied to the soil surface in each pot using a glass Cornwall syringe fitted with a Teejet SS8001E flat-fan nozzle (Spraying Systems Co., Wheaton, Ill. 60189-7900). For postemergence applications, the foliage of the test plants was sprayed using a DeVilbiss atomizer (DeVilbiss Health Car, Inc., Somerset, Pa. 15501) driven by compressed air at a pressure of 22 kPa. Untreated controls were included.

Pots were placed in the greenhouse following compound application. Pots from postemergence and preemergence were sub-irrigated and top-watered, respectively, as needed for the duration of the test. Visual injury ratings were taken 9 and 16 days after treatment for postemergence and preemergence applications, respectively, on a 0 to 100 scale where 0 represents no injury and 100 represents complete necrosis. Results are reported in Table I.

TABLE I

Phytotoxicity of methylidene mevalonate to several plant species in the greenhouse.

| Application | Rate kg ha$^{-1}$ | Visual Injury (%) | | | | | | | |
|---|---|---|---|---|---|---|---|---|---|
| | | HELAN | IPOHE | ECHCG | AVEFA | ABUTH | AMARE | SETFA | ALOMY |
| Postemergence[b] | 4.0 | 70 | 75 | 90 | 85 | 65 | 50 | 70 | 60 |
| | 2.0 | 60 | 65 | 70 | 60 | 60 | 40 | 50 | 60 |
| | 1.0 | 40 | 60 | 70 | 60 | 60 | 50 | 50 | 30 |
| | 0.5 | 30 | 60 | 60 | 40 | 40 | 30 | 40 | 30 |
| Preemergence | 4.0 | 60 | 20 | 30 | 10 | 30 | 40 | 30 | 30 |
| | 2.0 | 30 | 0 | 20 | 0 | 20 | 30 | 20 | 20 |
| | 1.0 | 30 | 0 | 0 | 0 | 0 | 0 | 0 | 0 |
| | 0.5 | 20 | 0 | 0 | 0 | 0 | 0 | 0 | 0 |

[b]Postemergence ratings taken 16 days after treatment.
At 21 days after treatment, all species were controlled 100% at 4.0 kg/ha

6. Evaluation of Herbicidal Activity

A. General Herbicidal Evaluation

Applications of methylidene mevalonate were made either to the foliage (postemergence) or soil (preemergence). Seeds of sunflower (*Helianthus annus*, HELAN), morningglory (*Ipomoea hederacea*, IPOHE) velvetleaf (*Abutilon theophrasti*, ABUTH), pigweed (*Amaranthus* spp., AMARE), barnyardgrass (*Echinochloa crusgalli*, ECHCG), giant foxtail (*Setaria faberi*, SETFA), wild oats (*Avena fatua*, AVEFA), and blackgrass (*Alopecurus myosuroides*, ALOMY) were planted in mineral soil (sandy clay loam, 51% sand, 26% silt, 23% clay, 2.8% O.M., pH 7.8) and Metro-mix (Bulk Sak, Inc., Malvern, Ark., USA) for preemergence and postemergence treatments, respectively. Pots receiving preemergence treatments were watered immediately following application. Prior to postemergence treatment, plants were grown in the greenhouse (16 h photoperiod, 27 C) and thinned to a density of 2 to 15 plants pot$^{-1}$, depending on species. At the time of postemergence applications, plants were 8-12 days old, 3 to 10 cm in height, and in the 1- to 3-true-leaf stage. Natural light in the greenhouse was supplemented with metal halide lights that provided an average photosynthetic photon flux of 500 μmol m$^{-2}$s$^{-1}$.

A sample of sodium methylidene mevalonate was dissolved in 4 mL of distilled water followed by 10 mL of formulation stock "B" (200 mL isopropanol, 20 mL crop oil concentrate, 0.4 g Triton X-155 [Sigma Chemical Co., St. Louis, Mo. 62718], and 78 mL water). This was followed by three 1:1 (v/v) serial dilutions using formulation stock "C" (100 mL isopropanol, 10 mL crop oil concentrate, 0.2 g Triton X-155, 390 mL water, 485 mL acetone and 15 mL DMSO).

Treatments were made at four different doses (4000, 2000, 1000, and 500 g ha$^{-1}$). For preemergence treatments, 1.75 mL

B. Post-Emergent Evaluation

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hr photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by serial dilution of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kilopascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. The results for methylidene mevalonate are reported in Table II. Species abbreviations as described for Table I with the following additions: soybean (*Glycine max*, GLXMA), rape (*Brassica napus*, BRSNN), chickweed (*Stellaria media*, STEME), cocklebur (*Xanthium strumarium* XANST), lambsquarters (*Chenopodium album*, CHEAL), violet (*Viola tricolor*, VIOTR), bindweed (*Polygonum convolvulus*, POLCO), spurge (*Euphorbia heterophylla*, EPHHL), Canada thistle (*Cirsium arvense*, CIRAR), corn (*Zea mays*, ZEAMX), rice (*Oryza sativa*, ORYSA), wheat (*Triticum aestivum*, TRZAS), crabgrass (*Digitaria sanguinalis*, DIGSA), shattercane (*Sorghum vulgare*, SORVU) and yellow nutsedge (*Cyperus esculentus*, CYPES).

TABLE II

Postemergent % Control with methylidene mevalonate

| Treated Species | Spray Concentration, ppm | | | | |
|---|---|---|---|---|---|
| | 2000 | 1000 | 500 | 250 | 125 |
| GLXMA | 80 | 80 | 50 | 20 | 20 |
| BRSNN | 60 | 50 | 50 | 10 | 0 |
| STEME | 40 | 20 | 0 | 0 | 0 |

TABLE II-continued

Postemergent % Control with methylidene mevalonate

| Treated Species | Spray Concentration, ppm | | | | |
|---|---|---|---|---|---|
| | 2000 | 1000 | 500 | 250 | 125 |
| XANST | 20 | 20 | 10 | 5 | 0 |
| CHEAL | 80 | 50 | 10 | 0 | 0 |
| IPOHE | 80 | 80 | 70 | 50 | 40 |
| AMARE | 100 | 100 | 100 | 30 | 10 |
| ABUTH | 60 | 50 | 20 | 5 | 0 |
| VIOTR | 30 | 25 | 0 | 0 | 0 |
| POLCO | 95 | 90 | 85 | 20 | 20 |
| EPHHL | 70 | 60 | 50 | 30 | 30 |
| CIRAR | 50 | 40 | 20 | 10 | 10 |
| BW ave | 63 | 54 | 37 | 15 | 11 |
| ZEAMX | 98 | 98 | 60 | 20 | 0 |
| ORYSA | 80 | 80 | 40 | 30 | 0 |
| TRZAS | 80 | 70 | 20 | 20 | 0 |
| ALOMY | 80 | 70 | 60 | 20 | 0 |
| AVEFA | 90 | 85 | 20 | 0 | 0 |
| ECHCG | 100 | 95 | 95 | 85 | 40 |
| DIGSA | 80 | 70 | 50 | 10 | 0 |
| SETFA | 90 | 80 | 70 | 70 | 30 |
| SORVU | 90 | 90 | 90 | 50 | 0 |
| GW ave | 88 | 82 | 64 | 39 | 12 |
| CYPES | 95 | 95 | 90 | 70 | 30 |

By applying the well-accepted probit analysis as described by J. Berkson in *Journal of the American Statistical Society*, 48, 565 (1953) and by D. Finney in "*Probit Analysis*" Cambridge University Press (1952), similar data can be used to calculate $GR_{80}$ values, which are defined as growth reduction factors that correspond to the effective dose of herbicide required to kill or control 80 percent of a target plant. Results for racemic mixtures, resolved enantiomers and the lactone of methylidene mevalonate are reported in Table III. Species abbreviations are as previously defined.

TABLE III

Herbicidal activity of the racemic mixtures and resolved enantiomers of methylidene mevalonate and the corresponding lactone. Values in the table are $GR_{80}$ values calculated from data gathered 15 days after treatment.

| Structure | g ae/ha | | | | | | | | |
|---|---|---|---|---|---|---|---|---|---|
| | STEME | VIOTR | ABUTH | DIGSA | CYPES | IPOHE | ECHCG | SORVU | SETFA |
| K+ salt | 2089 | 1768 | 720 | 1003 | 603 | 375 | <375 (98) | 400 | <375 (95) |
| Na+ salt | 1358 | 2290 | 965 | 774 | 375 | 416 | <375 (98) | <375 (93) | <375 (97) |
| K+ salt Chiral A(−) | >1500 | >1500 | >1500 | >1500 | >1500 | >1500 | >1500 | >1500 | >1500 |

TABLE III-continued

Herbicidal activity of the racemic mixtures and resolved enantiomers of methylidene mevalonate and the corresponding lactone.
Values in the table are $GR_{80}$ values calculated from data gathered 15 days after treatment.

| Structure | g ae/ha | | | | | | | | |
|---|---|---|---|---|---|---|---|---|---|
| | STEME | VIOTR | ABUTH | DIGSA | CYPES | IPOHE | ECHCG | SORVU | SETFA |
| [Structure: K+ salt, Chiral B(+)] | 1349 | 1865 | 1135 | 916 | 429 | 341 | 351 | 490 | 183 |
| [Structure: lactone] | 3032 | 2473 | 2266 | 834 | 834 | 725 | <375 (100) | 615 | 430 |

( ) Numbers in parenthesis are % growth reduction at the lowest rate tested.

C. Synergistic Herbicidal Activity

Methylidene mevalonate alone and in combination with nonanoic acid was applied to the foliage of rapidly growing plant material utilizing a track sprayer calibrated to deliver an application volume of 187 L/ha. These treatments were applied to both broadleaf and grass weed species. All treatments contained 1% crop oil concentrate. Assessment of herbicidal activity was performed visually relative to untreated controls after 14 days incubation in the greenhouse. Species abbreviations are as previously defined.

| Species | Methylidene mevalonate rate (g ae/ha) | Nonanoic Acid rate (g ae/ha) | Expected Injury % growth reduction | Actual Injury % growth reduction |
|---|---|---|---|---|
| AVEFA | 0 | 1120 | — | 0 |
| | 933 | 0 | — | 35 |
| | 933 | 1120 | 35 | 85 |
| CHEAL | 0 | 1120 | — | 0 |
| | 933 | 0 | — | 0 |
| | 933 | 1120 | 0 | 50 |
| DIGSA | 0 | 1120 | — | 0 |
| | 933 | 0 | — | 35 |
| | 933 | 1120 | 35 | 80 |
| IPOHE | 0 | 1120 | — | 0 |
| | 933 | 0 | — | 60 |
| | 933 | 1120 | 60 | 85 |

EXAMPLE 2

1. Culture of Microbial Strains.

Plugs of mycelia of strains *Fusarium* sp. DA056446 and *Nodulisporum* sp. DA092917 were grown on 30 ml agar media at 25° C. for 14 days. Strain DA056446 was grown on Malt Extract Agar (Becton Dickenson, Sparks, Md.) and strain DA092917 was grown on Oatmeal Agar (Becton Dickenson, Sparks, Md.). Mature cultures were overlayed with 30 ml 50% EtOH:$H_2O$, allowed to stand for 1 hour, and filtered through a 0.2 μm sterile filter. The filtered extracts were concentrated to ~3 ml under reduced pressure and analyzed both for the presence of methylidene mevalonate and for bioactivity.

2. Analysis of Extracts DA056446 and DA092917 for Methylidene Mevalonate.

The 10× concentrated extracts described above were analyzed by LC/MS using a graphitized carbon column chromatographic separation under conditions described in the table below. Detection was performed using full scan MS acquisition in a low cone voltage (30 V) positive ion electrospray ionization mode. Quantification utilized the area response of the m/z 125.0 ion signal, selective for methylidene mevalonate as the double water loss fragment of the $[M+H]^+$ molecular ion at m/z 161.

Sample Injection Volume: 15 μL

| Column: Hypercarb (100 × 4.6 mm; 5 μm) | | | | |
|---|---|---|---|---|
| | Percent Solvent | | Flow rate: 1 mL/minute | |
| Time (minutes) | Solvent A | Solvent B | Solvent | Solvent Description |
| 0 | 100 | 0 | A | 1% Formic acid[a] |
| 5 | 100 | 0 | B | Acetonitrile |
| 15 | 75 | 25 | | |
| 20 | 0 | 100 | | |
| 25 | 0 | 100 | | |
| 30 | 100 | 0 | | |
| 35 | 100 | 0 | | |

[a] 40 mL of 88% Formic acid in 4 L HPLC grade water

The sample originating from a 14 day fermentation of DA056446 was found to have a peak area of 2815 corresponding to a methylidene mevalonate concentration of 1.29 mg/L in the original 30 ml extract. The sample originating from a 14 day fermentation of DA092917 was found to have a peak area of 8712 corresponding to a concentration of 4.0 mg/L in the original 30 ml extract. The remaining amount of the 10× concentrated extract was forwarded for herbicide testing as described below.

3. Herbicidal Activity of Extracts DA056446 and DA092917.

Two ml of the 10× concentrated extract from each strain was taken to dryness under reduced pressure and redissolved in 75 ul of 50% MeOH:$H_2O$ containing 0.025% by volume of X-77 non-ionic surfactant. The solids in each tube was resuspended by vortex, and applied foliarly in ~2 ul droplets to HELAN (2 true leaf stage, 1.5-2.5 cm in height) and SETFA (2 true leaf stage, 2-3 cm in height). The plants had been grown in a greenhouse under conditions previously described in Example 1. For HELAN, 12 droplets (a total of 25 ul) were applied to each of two replicates. For SETFA, 5 droplets (a total of 10 ul) were applied to each of two replicates. The plants were allowed to dry and returned to the greenhouse where conditions were as described in Example 1. Plants were maintained by sub-irrigation for the duration of the study, and growth reduction was determined by comparison to untreated controls after 4 days. Average percent growth reductions were as follows:

|  | SETFA | HELAN |
|---|---|---|
|  | mean % growth reduction | |
| DA056446 culture extract | 75 | 75 |
| DA092917 culture extract | 95 | 90 |

What is claimed is:

1. A compound of Formula I:

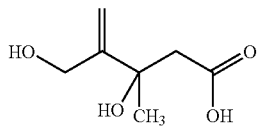

and
agriculturally acceptable salts, esters or amides and the lactone of the carboxylic acid and their enantiomers.

2. A composition comprising an herbicidaUy effective amount of a compound of Formula I:

(I)

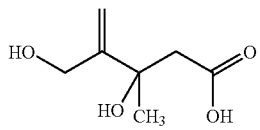

and
agriculturally acceptable salts, esters or amides and the lactone of the carboxylic acid and their enantiomers,
in admixture with an agriculturally acceptable adjuvant or carrier.

3. A method of controlling undesirable vegetation which comprises contacting the vegetation or the locus thereof or applying to the soil to prevent the emergence of vegetation with a herbicidally effective amount of a compound of Formula I:

(I)

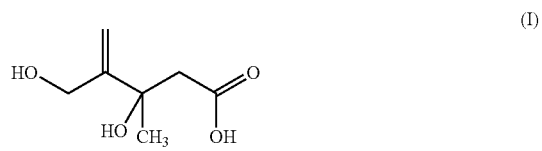

and
agriculturally acceptable salts, esters or amides and the lactone of the carboxylic acid and their enantiomers.

4. A synergistic herbicidal mixture comprising a compound of Formula I:

(I)

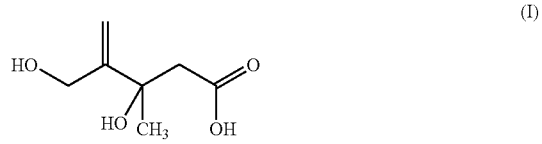

and
agriculturally acceptable salts, esters or amides and the lactone of the carboxylic acid and their enantiomers
and a $C_7$-$C_{22}$ alkanoic fatty acid.

* * * * *